(12) United States Patent
Gov-Ari (10) Patent No.: US 9,888,909 B2
(45) Date of Patent: Feb. 13, 2018

(54) ENDOSCOPIC-ENABLED TONGUE DEPRESSOR AND ASSOCIATED METHOD OF USE

(71) Applicant: The Curators of the University of Missouri, Columbia, MO (US)

(72) Inventor: Eliav Gov-Ari, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 14/079,265

(22) Filed: Nov. 13, 2013

(65) Prior Publication Data

US 2014/0180006 A1    Jun. 26, 2014

Related U.S. Application Data

(60) Provisional application No. 61/796,514, filed on Nov. 13, 2012.

(51) Int. Cl.
| | |
|---|---|
| *A61B 1/00* | (2006.01) |
| *A61B 13/00* | (2006.01) |
| *A61B 1/24* | (2006.01) |
| *A61M 16/04* | (2006.01) |

(52) U.S. Cl.
CPC .......... *A61B 13/00* (2013.01); *A61B 1/00135* (2013.01); *A61B 1/00154* (2013.01); *A61B 1/24* (2013.01); *A61M 16/0495* (2014.02)

(58) Field of Classification Search
USPC .......................... 600/120, 185, 190, 194–196
See application file for complete search history.

(56) References Cited

U.S. PATENT DOCUMENTS

| | | | |
|---|---|---|---|
| 2,969,059 A | | 1/1961 | Meek et al. |
| 4,112,936 A | * | 9/1978 | Blachly ........................ 128/861 |
| 4,198,970 A | * | 4/1980 | Luomanen ............... 128/207.15 |
| 4,213,451 A | | 7/1980 | Swenson |

(Continued)

FOREIGN PATENT DOCUMENTS

| | | |
|---|---|---|
| CN | 101836879 A | 9/2010 |
| DE | 102010026552 A1 | 1/2012 |
| EP | 2679145 A1 | 1/2014 |

OTHER PUBLICATIONS

"375116—McIvor Mouth Gags", Global Surgical Instruments, 1 page, retrieved from the Internet on Sep. 30, 2015, <http://www.globalsurgicalinstruments.com/375116>.

(Continued)

*Primary Examiner* — Matthew J Kasztejna
(74) *Attorney, Agent, or Firm* — Thompson Coburn LLP (57) ABSTRACT

The invention provides an endoscopic-enabled tongue depressor, as part of a mouth gag unit, with two-grooved design, where the first groove is for intubation, and the second groove accommodates the secure and adjustable placement of an optic device and associated method of use. The inventive tongue depressor enables full endoscopic procedures of the upper airway, such as nasopharynx, by providing a surgeon the ability to operate with both hands and an unobstructed view of a target area in the upper airway, in addition to real-time observation of the surgical field for other surgical staff (such as nursing staff, technicians, students and residents).

10 Claims, 7 Drawing Sheets

(56) References Cited

U.S. PATENT DOCUMENTS

| | | | | |
|---|---|---|---|---|
| 4,270,531 | A * | 6/1981 | Blachly | 128/207.14 |
| 4,306,547 | A * | 12/1981 | Lowell | 600/188 |
| 4,425,911 | A * | 1/1984 | Luomanen | 128/200.26 |
| 4,437,458 | A * | 3/1984 | Upsher | 600/193 |
| 4,491,435 | A | 1/1985 | Meier | |
| 4,495,945 | A * | 1/1985 | Liegner | 128/200.26 |
| 4,825,858 | A * | 5/1989 | Frankel | 128/200.26 |
| 5,038,766 | A * | 8/1991 | Parker | 128/200.26 |
| 5,069,206 | A * | 12/1991 | Crosbie | 128/207.17 |
| 5,174,283 | A * | 12/1992 | Parker | 128/200.26 |
| 5,203,320 | A * | 4/1993 | Augustine | 600/187 |
| 5,203,324 | A * | 4/1993 | Kinkade | 128/201.11 |
| 5,261,392 | A * | 11/1993 | Wu | 600/188 |
| 5,339,805 | A * | 8/1994 | Parker | 128/200.26 |
| 5,365,940 | A * | 11/1994 | Teves | 600/549 |
| 5,443,058 | A * | 8/1995 | Ough | A61B 1/267 600/188 |
| 5,590,643 | A * | 1/1997 | Flam | 128/200.26 |
| 5,649,540 | A * | 7/1997 | Alvarez et al. | 128/848 |
| 5,665,052 | A * | 9/1997 | Bullard | 600/194 |
| 5,800,344 | A * | 9/1998 | Wood, Sr. | A61B 1/267 600/185 |
| 5,840,013 | A * | 11/1998 | Lee et al. | 600/114 |
| 5,897,491 | A | 4/1999 | Kastenbauer et al. | |
| 6,257,238 | B1 * | 7/2001 | Meah | 128/859 |
| 6,293,908 | B1 * | 9/2001 | Fujikura et al. | 600/114 |
| 6,655,377 | B2 * | 12/2003 | Pacey | 128/200.26 |
| 6,718,970 | B2 * | 4/2004 | Sniadach | 128/200.26 |
| 6,955,645 | B1 * | 10/2005 | Zeitels | 600/187 |
| 6,966,319 | B2 * | 11/2005 | Fitton | 128/848 |
| 7,278,420 | B2 * | 10/2007 | Ganesh et al. | 128/200.26 |
| 7,735,489 | B2 * | 6/2010 | Mikkaichi et al. | 128/207.14 |
| 7,887,483 | B2 | 2/2011 | Rosenberg | |
| 7,909,757 | B2 * | 3/2011 | Herman | 600/190 |
| 8,202,215 | B2 * | 6/2012 | Xiao et al. | 600/194 |
| 8,297,973 | B2 * | 10/2012 | Hirsch et al. | 433/140 |
| 2005/0090712 | A1 * | 4/2005 | Cubb | 600/120 |
| 2010/0256451 | A1 * | 10/2010 | McGrath | A61B 1/267 600/185 |

OTHER PUBLICATIONS

"Davis-Crow Mouth Gags: MO 152", CareFusion—V. Mueller Catalog, 2 pages, retrieved from the Internet on Sep. 30, 2015, <https://catalog.carefusion.com/vmuelle/davis-crowe-mouth-gags-mo152.html>.

"Karl Storz Benjamin-Parsons Operating Laryngoscope", Medical Device Store, 2 pages, retrieved from the Internet on Sep. 30, 2015, <http://medicaldevicestor.com/store/t/ent/instruments/p/benjamin-parsons-operating-laryngoscope>.

International Search Report and Written Opinion for PCT/US2015/057768 dated Jan. 6, 2015.

Supplementary European Search Report for EP14847224 dated Apr. 28, 2017.

* cited by examiner

ENDOSCOPIC-ENABLED TONGUE DEPRESSOR AND ASSOCIATED METHOD OF USE

CROSS-REFERENCE TO RELATED APPLICATION

This patent application claims priority to U.S. Provisional Patent Application Ser. No. 61/796,514, filed Nov. 13, 2012, and entitled "Endoscopic-Enabled Tongue Depressor," the entire disclosure of which is incorporated herein by reference.

STATEMENT REGARDING FEDERALLY SPONSORED RESEARCH OR DEVELOPMENT

None.

FIELD OF INVENTION

The present invention relates to a medical and surgical device for performing examinations and treatments in the upper airway, more specifically, to an upgraded endoscopic gear with a high-definition fiber-optic camera.

BACKGROUND OF THE INVENTION

A routine ENT procedure, such as adenoidectomy, is performed under indirect, mirror-aided visualization. As a result, the surgical field, in most cases, is limited and not magnified. This prevents proper visualization of the surgical field and technique by a surgeon, operating room nursing staff, technicians, students and residents. In addition, the handheld mirror occupies a surgeon's non-operating hand, compromising the precision of a surgeon's work.

Figure 1:
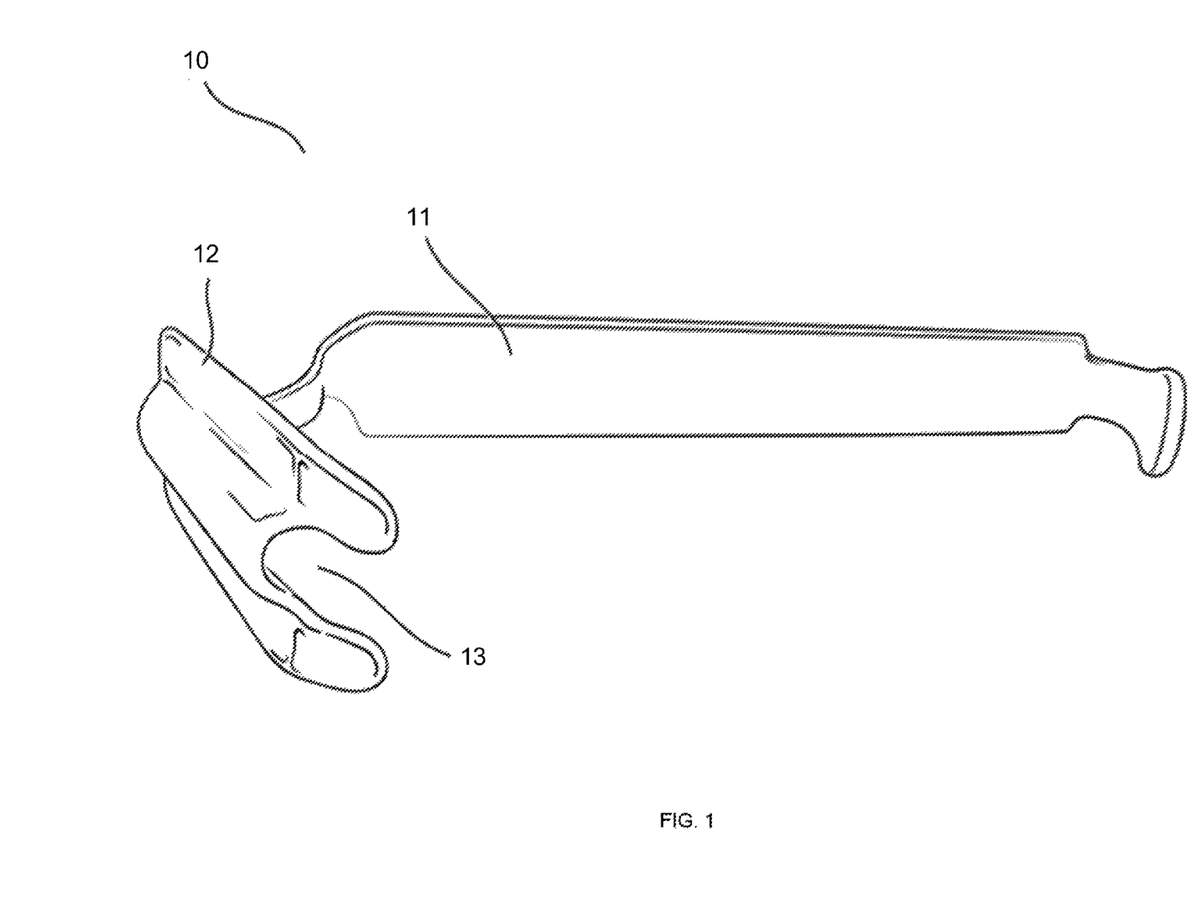
FIG. 1 illustrates a commercially available tongue depressor (Crowe-Davis tongue blade)

Currently, during routine ENT procedures, many different types/sizes of mouth gags are employed. The conventional mouth gag, such as the most commonly used Crowe-Davis and McIvor mouth gags, includes a mouth gag frame and an attachable tongue depressor, whereas the tongue depressor further comprises a tongue-covering blade and handle piece to attach to the mouth gag frame. Moreover, according to certain tongue depressor design, an accommodation for intubation has been made. For example, FIG. 1 illustrates a Crowe-Davis tongue depressor that comprises a rigid groove/indentation on the back portion of the tongue-covering blade for the passage of an intubation tube between the depressor and the tongue. However, no accommodation is made on any conventional tongue depressor for secure placement of an optic device, such as a fiber optic rigid or flexible scope. Rather, during contemporary upper airway procedures (such as the nasopharynx procedures), a handheld mirror is used by a surgeon, providing poor imaging quality and limited surgical field viewing.

Endoscopic technology has been increasingly sophisticated to provide high-definition visual monitoring during all sorts of surgical procedures. Several attempts to combine the endoscopic technology and the existing ENT devices, such as a mouth gag, have been developed and studied; however, most of them are rather cumbersome, and/or focused on developing the direct-line-of-sight from a surgeon's eye to the larynx of a patient, not suitable for adenoidectomy procedures, in which the adenoids are tucked away in the nasopharynx, located in the opposite direction, e.g., one hundred and eighty degrees (180°), from the larynx.

The present invention is directed to overcoming one or more of the problems set forth above.

SUMMARY OF INVENTION

The invention provides an endoscopic-enabled tongue depressor that may be attached to any suitable mouth gag frame, so as to provide a surgeon an unobstructed view of a target area in the upper airway (such as nasopharynx) of a patient and to allow a surgeon to utilize both hands during a procedure. The inventive device is a modified tongue depressor with certain accommodation for the secure and adjustable placement of an optic device, such as a rigid or flexible endoscope. The inventive tongue depressor, having a handle member and a tongue-covering member with a first groove/indentation to accommodate intubation tubing similar to an existing tongue depressor, further comprises a second groove/indentation to accommodate scope placement. The basic two-grooved design and elements of the inventive tongue-depressor, though illustrated mainly as a modified Crowe-Davis tongue-blade, may be employed/adopted to modify various existing tongue-blades in all types of mouth gags for upper airway procedures.

The inventive tongue depressor may employ several embodiments. For example, the foresaid second groove/indentation may be fully open (open barrel), fully enclosed (channel), or partially enclosed (enclosed at its proximal end while open at its distal end). The open barrel design allows the scope lens to be positioned and fixed at any distance along the tongue depressor. The enclosed channel design only affords the scope's working position at the very end of the tongue depressor, providing more secured fixation of the scope. The partially enclosed design allows the scope lens to be positioned and fixed at any distance along the open position of the groove and provides secured fixation of the scope at the same time.

Furthermore, the previously mentioned second groove/indentation may also adopt several different alignments in relation with the first groove/indentation. According to one embodiment, the second groove/indentation may be positioned parallel with the first groove/indentation and slightly off the midline of the tongue depressor. According to another embodiment, the second groove/indentation may be positioned on top of the first groove/indentation at the midline of the tongue depressor. According to yet another embodiment, the second groove/indentation may be positioned along an oblique course, so that its proximal end starts from the side, while its distal end converges toward the midline of the tongue depressor.

In an aspect of the invention, an apparatus for opening upper airway during an upper airway procedure with accommodations for both intubation and visualization is disclosed. The apparatus includes a tongue-covering member with a first groove/indentation on a back portion for placement of intubation tubing and a second groove/indentation on a top portion for placement of an optic means, wherein both grooves/indentations are in the longitude direction along the tongue-covering member, and the first groove is positioned around midline of the tongue-covering member, and a handle member attaching to the proximal end of the tongue-covering member.

In yet another aspect of the present invention is a method for opening upper airway during an upper airway procedure with accommodations for both intubation and visualization is disclosed. The method includes inserting a tongue-covering member of an endoscopic-enabled tongue depressor into a patient's mouth to cover the patient's tongue wherein a user operates a handle member of the endoscopic-enabled tongue depressor to insert the distal end of the tongue-covering member into the patient's mouth, wherein the tongue-covering member has a first groove/indentation on a back portion for placement of intubation tubing and a second groove/indentation on a top portion for placement of an optic means, wherein both grooves/indentations are in the longitude direction along the tongue-covering member and the first groove is positioned around midline of the tongue-covering member, wherein the handle member is attached to the proximal end of the tongue-covering member, placing a breathing tube through the first groove/indentation, placing the optic means through the second groove/indentation, rotating the optic means to adjust a viewing angle of the optical scope, and observing a target area in the upper airway.

These are merely some of the innumerable aspects of the present invention and should not be deemed an all-inclusive listing of the innumerable aspects associated with the present invention. These and other aspects will become apparent to those skilled in the art in light of the following disclosure and accompanying drawings.

BRIEF DESCRIPTION OF DRAWINGS

For a better understanding of the present invention, reference may be made to the accompanying drawings in which.

Reference characters in the written specification indicate corresponding items shown throughout the drawing figures.

DETAILED DESCRIPTION OF INVENTION

In the following detailed description, numerous exemplary specific details are set forth in order to provide a thorough understanding of the invention. However, it will be understood by those skilled in the art that the present invention may be practiced without these specific details, or with various modifications of the details. In other instances, well known methods, procedures, and components have not been described in detail so as not to obscure the present invention.

The invention provides an endoscopic-enabled tongue depressor, as part of a mouth gag, with certain accommodation for the secure and adjustable placement of an optic device (such as an endoscope). The inventive device comprises a two-grooved tongue-covering member, with a first groove/indentation for intubation and a second groove/indentation for optic observation (visualization), and a handle member for attaching the device to a mouth gag frame. The basic two-grooved design and elements of the inventive tongue-depressor may be employed/adopted to modify various existing tongue-blades in all types of mouth gags for upper airway procedures. The inventive tongue depressor employed in a mouth gag enables full endoscopic procedures of the upper airway by providing a surgeon 1) the ability to operate with both hands, 2) an unobstructed view of a target area in the upper airway, and 3) real-time observation of the surgical field for other surgical staff (such as nursing staff, technicians, students and residents).

FIG. 1 illustrates an example of a conventional tongue depressor, a commercially available Crowe-Davis tongue blade. As shown in FIG. 1, the conventional tongue depressor that is generally indicated by numeral 10 includes a handle piece 11 and a tongue-covering blade 12 with a groove/indentation/longitude cavity 13 along the midline of the back portion of the tongue-covering piece 12, whereas the handle piece 11 is attached to the tongue-covering blade 12 at its proximal end. During a procedure, the distal end of the tongue-covering piece 12 is inserted into a patient's mouth and placed onto the patient's tongue, while a breathing tube is placed through the groove 13 and down into the trachea.

Figure 2A:
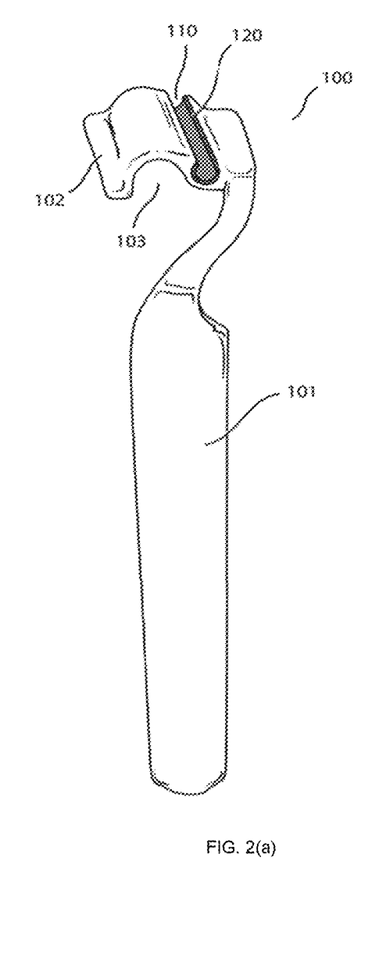
FIG. 2(a) illustrates an exemplary embodiment of the inventive tongue depressor, according to one embodiment of the invention.
Figure 2B:
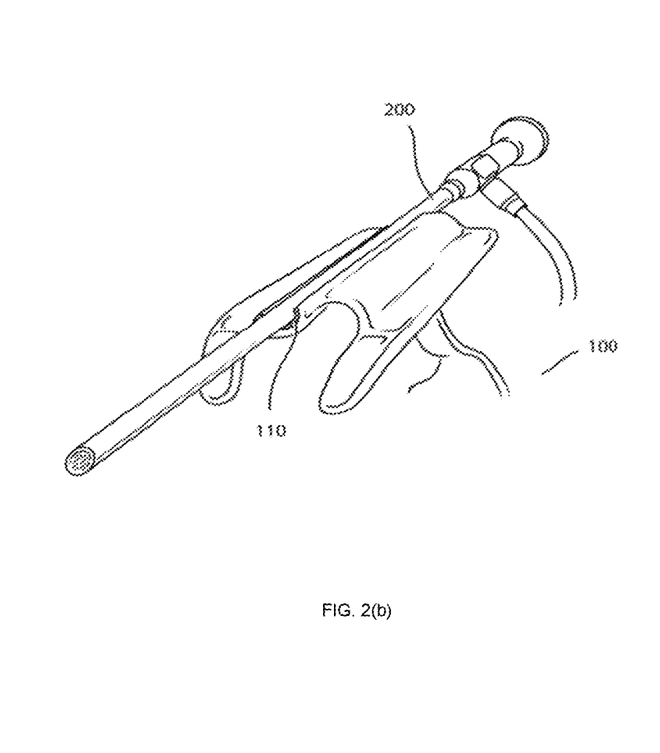
FIG. 2(b) illustrates the placement of a scope along the second groove/indentation of the inventive tongue depressor.

The inventive tongue depressor is modified upon the conventional tongue depressor to include an additional groove/indentation on a top portion of the tongue-covering piece to allow the secure and adjustable placement of an optic device (a scope). FIGS. 2(a) and 2(b) are illustrations of an exemplary embodiment of the inventive tongue depressor without and with a scope respectively. As shown in FIG. 2(a), the inventive tongue depressor is generally indicated by numeral 100, has a handle member 101, a tongue-covering member 102 with a first groove/indentation (the intubation groove) 103 on the back portion to accommodate intubation tubing, and a second groove/indentation (the scope groove) 110 on a top portion to accommodate scope placement and passage. It should be understood that the exemplary embodiment of the inventive tongue depressor can also be employed with any type of conventional tongue blade other than Crowe-Davis tongue blades. Preferably, the inventive tongue depressor 100 may also have an insulation liner 120, lined with the second groove/indentation, to prevent the heat generated by a scope to penetrate the tongue-covering member 102. As shown in FIG. 2(b), a scope 200 is placed through the second groove/indentation 110 of the inventive tongue depressor 100.

The inventive tongue depressor may employ several alternative designs. First, the foresaid second groove/indentation (the scope groove) may be fully open (open barrel), fully enclosed (channel), or partially enclosed (enclosed at its proximal end while open at its distal end). Second, the previously mentioned second groove/indentation (the scope groove) may also adopt several different alignments, such as parallel, positioned above, e.g., directly above, or oblique, in relationship with the first groove/indentation (the intubation groove).

Figure 3:
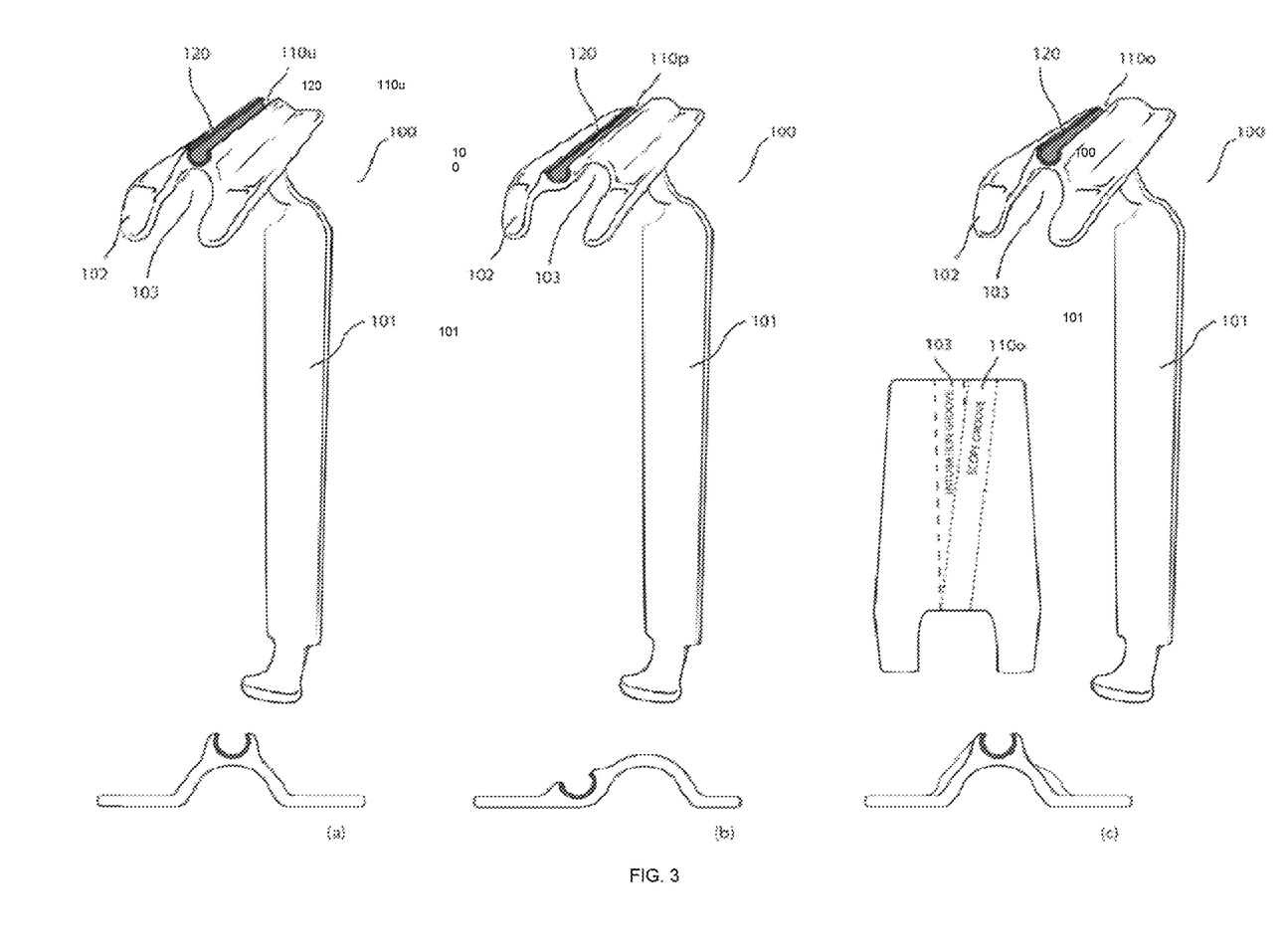
FIGS. 3(a) to 3(c) are illustrations (side view and front view of the tongue-covering member) of the inventive tongue depressor with an open barrel design.

FIGS. 3(a) to 3(c) are illustrations of the open barrel design with three alternative embodiments as to the alignment of the second groove/indentation (the scope groove). As shown in FIG. 3(a), the second groove/indentation (the scope groove) 110u is positioned on top of the first groove/indentation 103. The top placement of the second groove/ indentation (the scope groove) provides a midline placement of the scope with desired viewing angle for a clinician. However, the top placement may increase slightly the bulkiness (height) of the tongue-covering member in the midline, which may reduce the surgical field in certain cases (such as in infants and young children when the surgical field is limited).

Also shown in FIG. 3(b), the second groove/indentation (the scope groove) 110p is positioned parallel to the first groove/indentation (the intubation groove) 103 and slightly off the midline of the tongue-covering member 102. The slight deviation from the midline, in most cases, will not distort a surgeon's viewing angle, while the tongue-covering member is less bulky in this alignment. However, it should be understood that the location of the second groove/indentation (the scope groove) 110p can be either side of the first groove/indentation (the intubation groove) 103 and not limited to a specific location as depicted in FIG. 3(b).

As shown in FIG. 3(c), the second groove/indentation (the scope groove) 110o is positioned oblique to the first groove/indentation (the intubation groove) 103, whereas the proximal end of the second groove/indentation (the scope groove) 110o starts at the side (off midline) of the tongue-covering member 102 and the distal end of the second groove/indentation (the scope groove) 110o slants to the midline of the tongue-covering member 102 on top of the first groove/indentation (the intubation groove) 103. FIG. 3(c) also provides a top view of the oblique alignment, which illustrates the alignment of the second groove/indentation (the scope groove) 110o in relationship with the first groove/indentation (the intubation groove) 103. The oblique alignment provides preferred midline viewing angle and reduces the bulkiness of the tongue-covering member. However, it should be understood that the proximal end of the second groove/indentation (the scope groove) 110p can be positioned oblique to either side of the first groove/indentation (the intubation groove) 103 and is not limited to a specific location as depicted in FIG. 3(b).

FIGS. 4(a) to 4(c) are illustrations of an exemplary embodiment of the inventive tongue depressor in the enclosed channel design. FIG. 4(a) illustrates an exemplary embodiment of the inventive tongue depressor in the enclosed channel design having the second groove/indentation (the scope groove) 110u positioned above, e.g., directly above, the first groove/indentation (the intubation groove) 103. FIG. 4(b) illustrates an exemplary embodiment of the inventive tongue depressor in the enclosed channel design having the second groove/indentation (the scope groove) 110p positioned parallel to the first groove/indentation (the intubation groove) 103. FIG. 4(c) illustrates an exemplary embodiment of the inventive tongue depressor in the enclosed channel design having the second groove/indentation (the scope groove) 110o positioned oblique to the first groove/indentation (the intubation groove) 103.

Figure 4:
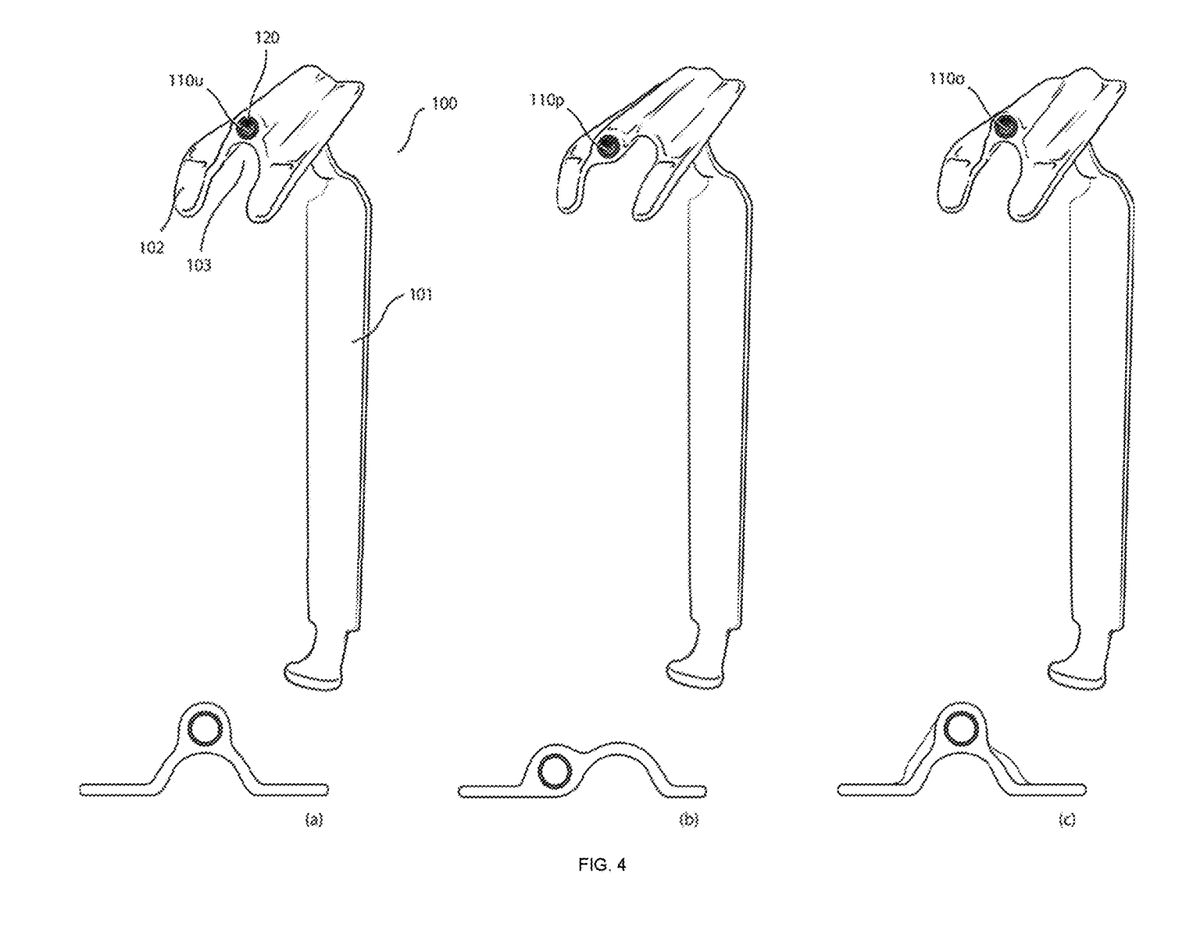
FIGS. 4(a) to 4(c) are illustrations (side view and front view of the tongue-covering member) of the inventive tongue depressor with an enclosed-channel design.
Figure 5:
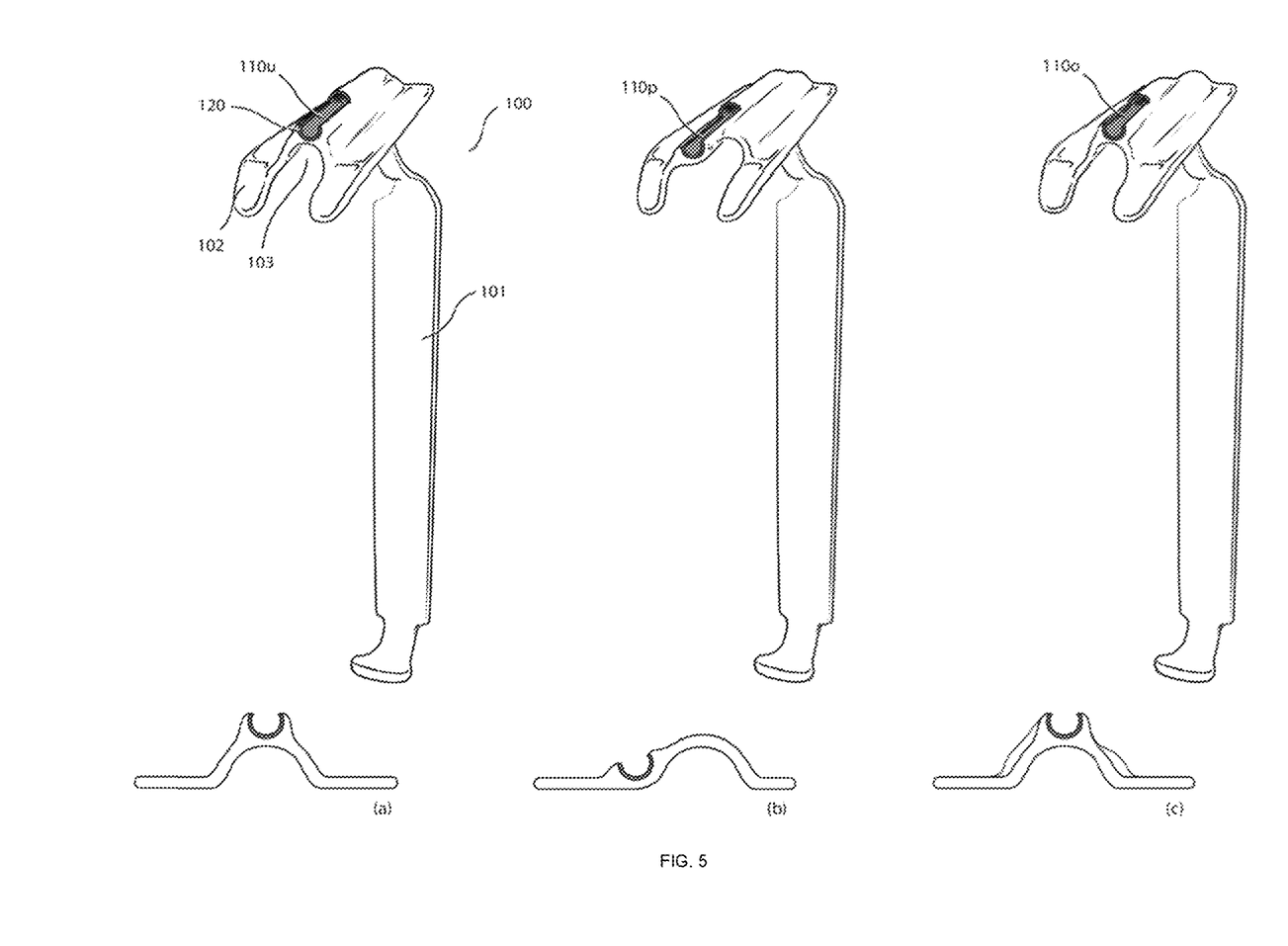
FIGS. 5(a) to 5(c) are illustrations (side view and front view of the tongue-covering member) of the inventive tongue depressor with a partially enclosed design.

FIGS. 5(a) to 5(c) are illustrations of an exemplary embodiment of the inventive tongue depressor in the partially enclosed design. FIG. 5(a) illustrates an exemplary embodiment of the inventive tongue depressor in the partially enclosed design having the second groove/indentation (the scope groove) 110u positioned above, e.g., directly above, the first groove/indentation (the intubation groove) 103. FIG. 5(b) illustrates an exemplary embodiment of the inventive tongue depressor in the partially enclosed design having the second groove/indentation (the scope groove) 110p positioned parallel to the first groove/indentation (the intubation groove) 103. FIG. 5(c) illustrates an exemplary embodiment of the inventive tongue depressor in the partially enclosed design having the second groove/indentation (the scope groove) 110o positioned oblique to the first groove/indentation (the intubation groove) 103. As shown in FIGS. 4 and 5, the channel design and partially covered design also may adopt three different groove alignments.

Figure 6:
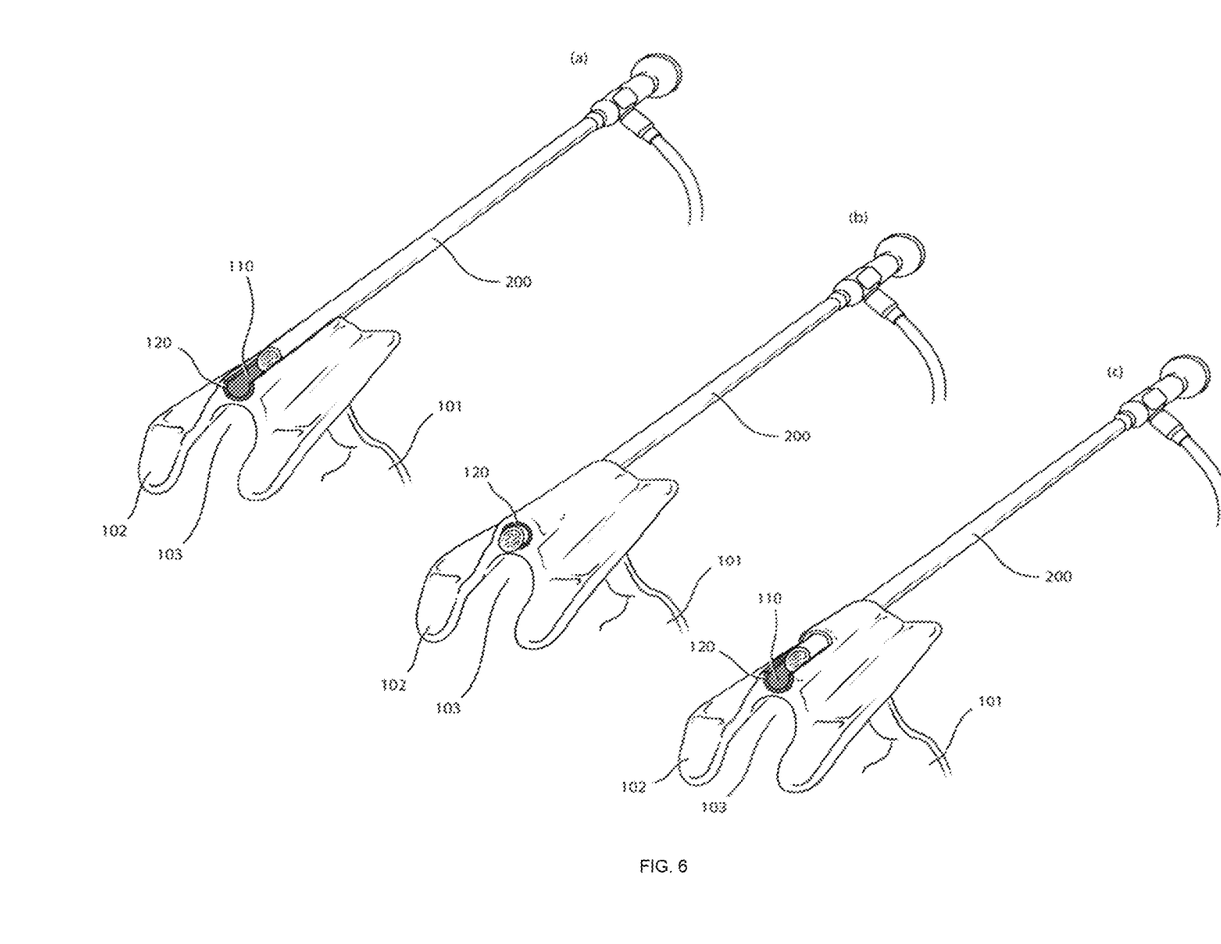
FIGS. 6(a) to 6(c) are illustrations of the scope placements in three different designs.

FIGS. 6(a) to 6(c) are illustrations of the exemplary scope placements in three different designs. As shown in FIG. 6(a), the open barrel design allows the most flexibility on the scope placement, i.e., the scope lens may be positioned and fixed at any distance along the tongue depressor, besides the distal end and beyond. As shown in FIG. 6(b), the enclosed channel design only allows the scope's working position at the distal end of the tongue depressor and beyond, though it provides more secured fixation of the scope. Moreover, the channel design is relatively bulky compared to the open barrel design. Still as shown in FIG. 6(c), the partially enclosed design, a hybrid design, allows the scope lens to be positioned and fixed at any distance along the open portion of the groove and provides secured fixation of the scope at the same time.

In the preferred embodiment, the size/width of the second groove/indentation (the scope groove) may vary to fit a particular size of a scope. Likewise, the first groove/indentation may vary to fit a particular size of a breathing tube.

In another embodiment, for the secure fixation of a scope, the insulation liner may be made of a material that provides a secured fitting, e.g., snug fitting, for the scope, so that the scope may be adjusted along the groove but held in place after the adjustment. It should be understood that any applicable type of material that can serve as a secure means can be used in this embodiment.

In another embodiment, an additional positioning means can be employed to further secure a scope. For example, an O-ring stopper can be used to secure the scope positioned in the second groove/indentation (the scope groove). In this embodiment, the positioning means may be employed at the proximal end of the second groove/indentation. Alternatively, an additional support means can be employed to provide adjustable support to the scope. Preferably, the support means can comprise any conventional adjustable support fixtures which can be removably attached to the tongue-covering member and/or handle member to support the scope so as to stably hold the scope.

Figure 7:
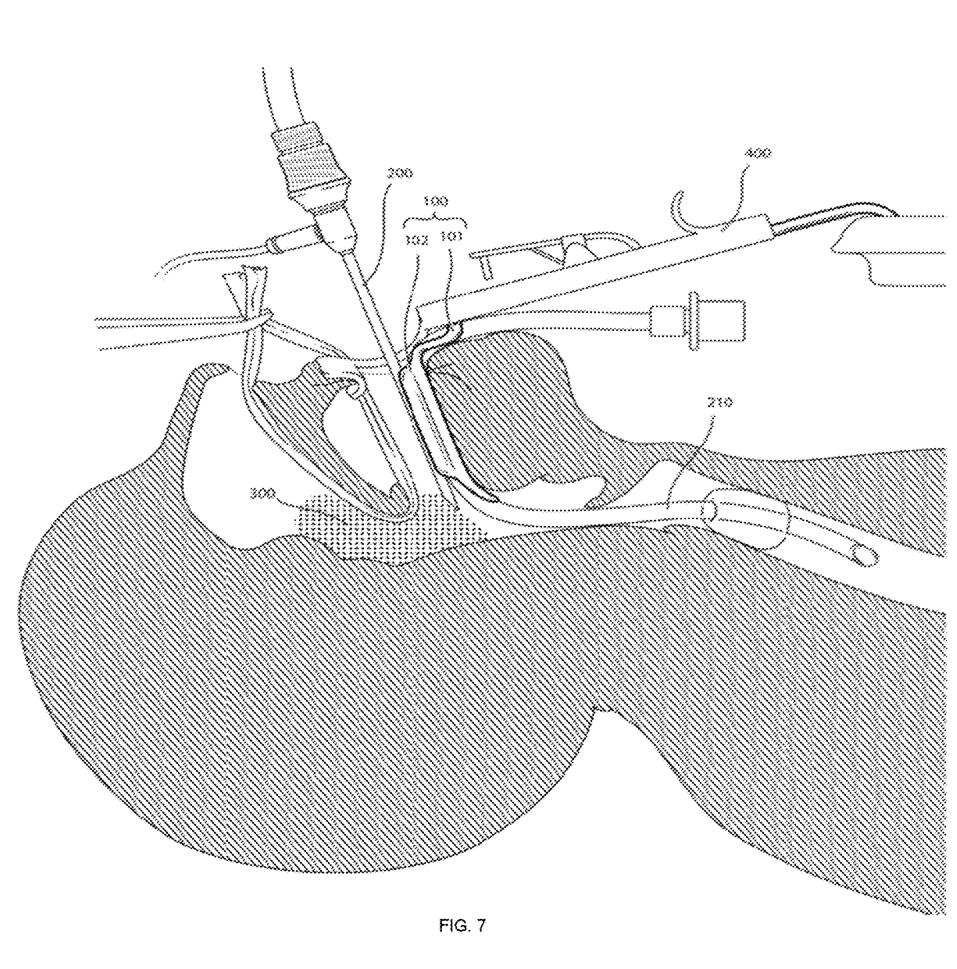
FIG. 7 illustrates an exemplary embodiment of the inventive tongue depressor engaging in an upper airway procedure.

FIG. 7 is an illustration of an exemplary inventive tongue depressor attached to a mouth gag frame and employed in an upper airway procedure. As shown in FIG. 7, the handle member 101 of the inventive tongue depressor 100 is secured on the mouth gag frame 400, while the tongue-covering member 102 is inserted into a patient's mouth covering the patient's tongue. The breathing tube 210 is placed through the first groove/indentation, while the scope 200 is placed along the second groove/indentation. By sliding or rotating the scope 200, the viewing angle 300 may be adjusted accordingly to view the desired palatal area.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth.

The invention claimed is:

1. An apparatus for opening upper airway during an upper airway procedure with accommodations for both intubation and visualization comprising: a tongue-covering member configured to be inserted into a patient's mouth, said tongue-covering member having a first groove/indentation on a back portion for placement of intubation tubing and a second groove/indentation on a top portion for placement of an optic means, wherein both grooves/indentations are in the longitude direction along the entirety of said tongue-covering member, wherein said second groove/indentation is a partially enclosed design that is enclosed at a proximal end while open at a distal end, wherein said back portion is configured to be placed in direct contact with a patient's tongue and said top portion is configured to be facing an upper airway of the patient's mouth, said first groove/indentation facing the patient's tongue so that intubation tubing placed within the first groove/indentation is secured solely within the first groove/indentation and configured for direct contact of the patient's tongue onto each the back portion and the placed intubation tubing; and a handle member attaching to the proximal end of said tongue-covering member and securable to a mouth gag frame while said tongue-covering member is inserted into said patient's mouth.

2. The apparatus for opening upper airway during an upper airway procedure with accommodations for both intubation and visualization as set forth in claim 1, wherein said second groove/indentation is positioned on top of said first groove/indentation.

3. The apparatus for opening upper airway during an upper airway procedure with accommodations for both intubation and visualization as set forth in claim 1, wherein said second groove/indentation is positioned parallel to said first groove/indentation.

4. The apparatus for opening upper airway during an upper airway procedure with accommodations for both intubation and visualization as set forth in claim 1, wherein said second groove/indentation is positioned oblique to said first groove/indentation.

5. The apparatus for opening upper airway during an upper airway procedure with accommodations for both intubation and visualization as set forth in claim 1, further comprising a liner located along said second groove/indentation.

6. The apparatus for opening upper airway during an upper airway procedure with accommodations for both intubation and visualization as set forth in claim 5, wherein said liner is a heat insulator liner.

7. The apparatus for opening upper airway during an upper airway procedure with accommodations for both intubation and visualization as set forth in claim 5, wherein said liner comprises a material that provides a secured fitting for said optic means.

8. The apparatus for opening upper airway during an upper airway procedure with accommodations for both intubation and visualization as set forth in claim 1, wherein size and width of said second groove/indentation can vary to fit a particular size of said optic means.

9. The apparatus for opening upper airway during an upper airway procedure with accommodations for both intubation and visualization as set forth in claim 1, further comprising a positioning means at the proximal end of said second groove/indentation for securing said optic means.

10. The apparatus for opening upper airway during an upper airway procedure with accommodations for both intubation and visualization as set forth in claim 1, further comprising a supporting means providing adjustable support to said optic means, wherein said supporting means can be removably attached to said tongue-covering member and said handle member.

* * * * *